United States Patent [19]

Ichii et al.

[11] Patent Number: 5,626,854
[45] Date of Patent: May 6, 1997

[54] BATH COMPOSITION

[75] Inventors: Yuji Ichii; Norihiro Tanaka; Shinobu Mori; Hidenori Yorozu, all of Tochigi, Japan

[73] Assignee: Kao Corporation, Tokyo, Japan

[21] Appl. No.: 405,961

[22] Filed: Mar. 17, 1995

[30] Foreign Application Priority Data

Mar. 17, 1994 [JP] Japan ................... 6-047181
Mar. 18, 1994 [JP] Japan ................... 6-048497

[51] Int. Cl.$^6$ ........................................ A61K 7/00
[52] U.S. Cl. ................ 424/401; 424/195.1; 424/715
[58] Field of Search .................. 424/401, 195.1, 424/715

[56] References Cited

U.S. PATENT DOCUMENTS

| | | | |
|---|---|---|---|
| 4,670,185 | 6/1987 | Fujiwara et al. | 252/311 |
| 4,795,638 | 1/1989 | Ayache et al. | 424/195.1 |
| 5,053,433 | 10/1991 | Philippossian et al. | 424/47 |
| 5,141,666 | 8/1992 | Yorozu et al. | 252/174.14 |
| 5,165,935 | 11/1992 | Andre | 424/450 |
| 5,182,105 | 1/1993 | Takata et al. | 424/78.02 |
| 5,194,259 | 3/1993 | Soudant et al. | 424/401 |
| 5,470,579 | 11/1995 | Bonte et al. | 424/450 |
| 5,478,501 | 12/1995 | Rau | 252/547 |

*Primary Examiner*—Amy Hulina
*Attorney, Agent, or Firm*—Oblon, Spivak, McClelland, Maier & Neustadt, P.C.

[57] ABSTRACT

A bath composition is disclosed, which comprises a xanthine derivative or a β-adrenergic stimulants. The bath composition, as dissolved in bath water, gives a moist (fresh) feel to the skin and a warm feel to the body. A method for imparting a moist feel to the skin and improving a warm feel of the body is also disclosed.

10 Claims, No Drawings

BATH COMPOSITION

FIELD OF THE INVENTION

This invention relates to a bath composition giving a moist feel (a fresh feel) to the skin and a warm feel to the body.

BACKGROUND OF THE INVENTION

Bathing not only cleans one's body but warms the entire body, producing various effects such as mental relaxation, and is an action indispensable to a daily life.

There are many people who suffer from loss of sebum from the skin due to bathing, particularly skin dryness after taking a bath in winter. To alleviate the skin dryness, they usually apply various skin care goods, such as lotions or creams, after bathing. However, application of skin care goods is troublesome, and especially for those of advanced age it is hard to apply skin care goods sufficiently to all over their body.

In the circumstance, it has been proposed to incorporate an oily component into a bath agent thereby preventing skin from getting dryness after bathing. Further, bath agents mainly composed of various inorganic salts or hot spring components have been developed aiming at increase in bathing effects, for example, recovery from fatigue and an improved warm feel.

However, the above-mentioned bath agent containing an oily component cannot be said to give a bather a satisfactory moist feel of the skin and a sufficient warm feel of the body, and it has been still in demand to develop a bath agent excellent in providing a moist feel of the skin and a warm feel of the body.

SUMMARY OF THE INVENTION

As a result of extensive investigations, the present inventors have found that a bath composition containing a xanthine derivative and/or a β-adrenergic stimulant brings about excellent bathing effects of giving a moist feel to the skin and a warm feel to the body. The present invention has been completed based on these finding.

Namely, the present invention provides a bath composition comprising a xanthine derivative or a β-adrenergic stimulant.

The present invention is also provides a method for imparting a moist feel to the skin and improving a warm feel of the body which comprises bathing the body in a bath containing a bathing composition comprising a xanthine derivative and/or a β-adrenergic stimulant in an amount effective to achieve the functions of imparting a moist feel to the skin and improving a warm feel of the body.

DETAILED DESCRIPTION OF THE INVENTION

The xanthine derivative which can be used in the present invention is not particularly limited and it may be one chemically synthesized or isolated in a substantially pure form from a plant. Typical examples of the xanthine derivatives include those represented by formula (I):

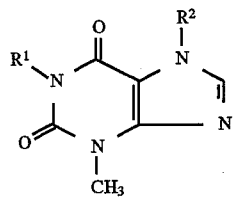

wherein $R^1$ represents a methyl group or a hydrogen atom; $R^2$ represents a hydrogen atom or an alkyl group having 1 to 12 carbon atoms which may be substituted by one or two hydroxyl groups or alkanoyl groups having 2 to 10 carbon atoms, and salts thereof.

Specific examples of the xanthine derivative of formula (I) are xanthine, aminophylline, theophylline, choline theophylline, caffeine, theobromine, oxtriphylline, diprophylline, and proxyphylline. These xanthine derivatives may be used either individually or as a combination of two or more thereof. In the present invention, it is preferable to use at least one compound selected-from the group consisting of aminophylline, theophylline, and caffeine.

The xanthine derivative is preferably added in an amount of 0.05% by weight or more, more preferably from 0.1 to 20% by weight, based on the total composition. The xanthine derivative to be used may be a synthetic compound or a compound isolated in a substantially pure form from a plant, such as leaves of a tea plant. Leaves of a tea plant, for example, contains caffeine and traces of theobromine, theophylline, xanthine, etc., but if used as a crude drug (as dried leaves or an extract thereof), the amount necessary for obtaining sufficient bathing effects would be so large, making the bath water smell of the tea leaves. Moreover, such a large amount of tea leaves is very bulky and inconvenient for use.

The β-adrenergic stimulant which can be used in the present invention is not particularly limited. Examples of suitable β-adrenergic stimulants include isoproterenol, epinephrine, dl-norepinephrine, dobutamine, dopamine, butopamine, salbutamol, terbutaline, isoetarine, protokylol, fenoterol, metaproterenol, clorprenaline, hexoprenaline, trimethoquinol, procaterol hydrochloride, prenalterol, forskolin, disodium (R,R)-5-[2-[[2-(3-chlorophenyl)-2-hydroxyethyl]amino]propyl]-1,3-benzodioxol-2,2-dicarboxylate, (R*, R*)-4-[2-({2-[(3-chlorophenyl)-2-hydroxyethyl]-amino}propyl) phenyl]phenoxyacetic acid, {2-hydroxy-5-[2-({2-hydroxy-3-[4-(1-methyl-4-trifluoromethyl)-1H-imidazol-2-yl]phenoxy}propyl)amino]ethoxy}benzamide monomethane-sulfonate, and erythro-DL-1-(7-methylindan-4-yloxy)-3-isopropylaminobutan-2-ol, and pharmaceutically acceptable salts thereof. The pharmaceutically acceptable salts include acid addition salts, metal salts, ammonium salts, organic amine addition salts, and amino acid addition salts. In the present invention, it is preferred to use at least one of β-adrenergic stimulants selected from isoproterenol, dobutamine, salbutamol, and pharmaceutically acceptable salts thereof.

The β-adrenergic stimulant is preferably added in an amount of 0.005% by weight or more, more preferably from 0.01 to 20% by weight, based on the total composition.

The xanthine derivative and the β-adrenergic stimulant may be used in combination. In this case, they are used in the bath composition in a weight ratio of the xanthine derivative to the β-adrenergic stimulant of 1/10 to 10/1 and in the total amount of 0.01 to 20% by weight based on the total weight of the composition. By using the xanthine derivative and the β-adrenergic stimulant in combination, the warm feel obtained by the bath composition according to the present invention can sustain long.

The moist feel on the skin and the warm feel in the body obtained by the bath composition according to the present invention can be enhanced by using inorganic salts in combination.

Preferred examples of the inorganic salt to be combined include chlorides such as sodium chloride and potassium chloride; carbonates such as sodium hydrogen-carbonate, sodium carbonate, potassium hydrogencarbonate, calcium carbonate, magnesium carbonate, and sodium sesquicarbonate; borax; sulfates such as sodium sulfate; sulfides such as sodium sulfide and potassium sulfide; nitrates such as sodium nitrate; thiosulfates such as sodium thiosulfate; phosphates such as sodium polyphosphate and sodium phosphate; oxides such as calcium oxide and magnesium oxide. Among them, sodium chloride, sodium hydrogen-carbonate, sodium carbonate, sodium sulfate, sodium sesquicarbonate, magnesium oxide, calcium carbonate, and magnesium carbonate are more preferred.

The inorganic salt is used in the bath composition in an amount to give a concentration in bath water of preferably 10 to 2,000 ppm, more preferably 10 to 400 ppm. In practical, the inorganic salt may be incorporated in the bath composition in an amount of preferably 5% by weight or more, more preferably 10% by weight or more, based on the total bath composition and also at a weight ratio of preferably from 0.25 to 2,000, more preferably from 0.5 to 1,000, to the xanthine derivative or at a weight ratio of preferably from 0.25 to 20,000, more preferably from 0.5 to 10,000, and furthermore preferably from 0.5 to 1,000, to the $\beta$-adrenergic stimulant.

Where the bath composition contains the carbonate as the inorganic salt, it is preferred to add to the composition an acid component for rendering bath water weakly acidic (preferably pH 5 to 7, more preferably pH 6 to 6.7) so that the composition may evolve carbon dioxide when added to bath water. In this case, the carbon dioxide evolved is dissolved in bath water, and the dissolved carbon dioxide exerts a blood circulation stimulating effect, whereby the moist feel on the skin and the warm feel in the body obtained by the bath composition according to the present invention are further enhanced. While the acid component to be added is not particularly limited, it is preferable to use an organic acid in excess to the carbonate.

Suitable examples of the organic acid to be combined with the carbonate include succinic acid, fumaric acid, malic acid, tartaric acid, citric acid, and benzoic acid. These organic acids may be used either individually or as a combination of two or more thereof. In the present invention, it is preferred to use a carbonate selected from sodium hydrogencarbonate, sodium carbonate, sodium sesquicarbonate, and magnesium carbonate and an organic acid selected from succinic acid and fumaric acid.

The carbonate and the organic acid may be used in amounts sufficient to evolve the carbon dioxide gas in bath water at a carbon dioxide gas concentration of 60 ppm or more. In practical, the carbonate may preferably be used in an amount of 5 to 80% by weight, more preferably from 10 to 50% by weight, based on the total bath composition. On the other hand, the organic acid is preferably used in an amount of 10 to 300% by weight, more preferably from 30 to 150% by weight, based on the cabonate.

It is also preferred that a weight ratio of the carbonate to the xanthine derivative is from 0.25 to 1,600, more preferably from 0.5 to 500, while a weight ratio of the carbonate to the $\beta$-adrenergic stimulant is preferably from 0.25 to 16,000, more preferably from 0.5 to 5,000, furthermore preferably from 0.5 to 500.

Moreover, the moist feel on the skin and the warm feel in the body obtained by the bath composition according to the present invention can further be enhanced by using an oily component in combination with the xanthine derivative and/or the $\beta$-adrenergic stimulant.

Examples of the oily component include fats and oils, waxes, hydrocarbons, higher fatty acids, higher alcohols, esters, essential oils, and silicone oils.

Examples of the fats and oils include natural fats and oils, such as soybean oil, bran oil (rice polishing oil), jojoba oil, avocado oil, almond oil, olive oil, cacao oil, sesame oil, persic oil (apricot karnel oil), castor oil, palm oil, mink oil, tallow, and lard; hardened oils obtained by hydrogenation of these natural fats and oils; and synthetic triglycerides, such as trimyristin and glyceryl tri(2-ethylhexanoate). Examples of the wax include carnauba wax, whale wax, bees wax, and lanolin. Examples of the hydrocarbon include liquid paraffin, vaseline, paraffin microcrystalline wax, ceresin, squalane, and pristane. Examples of the higher fatty acid include lauric acid, myristic acid, palmitic acid, stearic acid, behenic acid, oleic acid, linoleic acid, linolenic acid, lanolin fatty acid, and isostearic acid. Examples of the higher alcohol include lauryl alcohol, cetyl alcohol, stearyl alcohol, oleyl alcohol, lanolin alcohol, cholesterol, and 2-hexyldecanol. Examples of the ester include cetyl octanoate, glyceryl trioctanoate, myristyl lactate, cetyl lactate, isopropyl myristate, myristyl myristate, octyldodecyl myristate, isopropyl palmitate, isopropyl adipate, butyl stearate, decyl oleate, cholesteryl isostearate, and polyoxyethylene (POE) sorbitol fatty acid ester. Examples of the essential oil include mentha oil, jasmine oil, camphor oil, hinoki oil, orange peel oil, ryu oil, turpentine oil, cinnamon oil, bergamot oil, mandarin oil, calamus oil, pine oil, lavender oil, bay oil, clove oil, hiba oil, rose oil, eucalyptus oil, lemon oil, thyme oil, peppermint oil, sage oil, menthol, cineole, eugenol, citral, citronellal, borneol, linalool, geraniol, camphor, thymol, spilanthol, pinene, limonene, and terpene compounds. Examples of the silicone oil include dimethylpolysiloxane. These oily components may be used either individually or as a combination of two or more thereof. In the present invention, it is preferred to use glyceryl myristate, glyceryl tri-(2-ethylhexanoate), lanolin, liquid paraffin, vaseline, paraffin microcrystalline wax, squalane, lauric acid, myristic acid, palmitic acid, linoleic acid, linolenic acid, isostearic acid, cetyl alcohol, stearyl alcohol, oleyl alcohol, cholesterol, cetyl octanoate, glyceryl trioctanoate, isopropyl myristate, octyldodecyl myristate, cholesterol isostearate, POE sorbitol fatty acid esters, mentha oil, orange peel oil, cinnamon oil, rose oil, menthol, cineole, eugenol, citral, citronellal, geraniol, pinene, limonene, and dimethylpolysiloxane.

The content of the oily component in the bath composition is selected appropriately according to the dose form of the bath composition and preferably an amount to give a concentration in bath water of 10 to 500 ppm, more preferably an amount to give a concentration in water of 10 to 100 ppm. In practical, the amount of the oily component may usually range from 0.1 to 95% by weight based on the total composition. A weight ratio of the oily component to the xanthine derivative is preferably from 0.005 to 1,900, more preferably from 0.005 to 950, while a weight ratio of the oily component to the $\beta$-adrenergic stimulant is preferably from 0.005 to 19,000, more preferably from 0.005 to 9,500, furthermore preferably from 0.005 to 950.

If desired, the bath composition of the present invention may further contain a dispersant or an emulsifying agent for the oily components.

A dispersant or emulsifying agent serves to prevent the oily components in the composition from floating onto the surface of the bath water and also to opacity the bath water to a degree of visibility of not more than 40 cm depth, preferably not more than 20 cm depth, in a 0.01% aqueous solution thereby offering the luxury appearance like a milk bath.

Such a dispersant or emulsifying agent includes water-soluble high polymers and surfactants. Examples of the water-soluble high polymers are sodium alginate, propylene glycol alginic ester, gum arabic, xantham gum, pectin, tragacanth gum, sodium carboxymethyl cellulose, methyl cellulose, carboxyvinyl polymer, polyethylene glycol, polyvinyl alcohol, polyvinylpyrrolidone, milk protein, soybean protein, gelatin, egg protein, sodium casein, and whey protein; with gums, such as gum arabic and xantham gum, and water-soluble proteins, such as sodium casein and whey protein, being preferred.

Examples of the surfactant include anionic surfactants, cationic surfactants, and nonionic surfactants, either natural or synthetic. Taking irritation to the skin into consideration, nonionic surfactants are preferred.

Examples of the nonionic surfactant include glycerin fatty acid esters, propylene glycol fatty acid esters, sorbitan fatty acid esters, polyoxyethylene sorbitan fatty acid esters, polyoxyethylene sorbitol tetraoleate, polyoxyethylene alkyl ethers, polyoxyethylene polyoxypropylene glycol, polyoxyethylene polyoxypropylene alkyl ethers, polyethylene glycol fatty acid esters, polyoxyethylene castor oil, polyoxyethylene hardened castor oil, and polyglycerin fatty acid esters.

These dispersants or emulsifying agents may be used either individually or as a combination of two or more thereof in a total amount of from 5 to 100% by weight based on the aforesaid oily components.

The bath composition of the present invention may furthermore contain various other components conventionally employed in the art. Illustrative but non-limiting examples of the other components which may be used in the present invention include (a) inorganic acids, such as boric acid, metasilicic acid, and silicic anhydride; (b) crude drugs, such as fennel, chamomile flower, ginkgo, phellodendron, cinnamon bark, safflower, peony radix, ginger, sweet flag (calamus), *Cnidii Rhizoma*, angelica radix (*Angelicae Radix* and *Angelicae Dahuricae Radix*), orange peel (*Citrus unchu* Macrovith or *Citrus aurantium* L.), *Atractylodis Lanceae* rhizoma, valerian radix, Japanese mint (*Mentha arvensis*), hoelen, and ginseng; (c) coloring matter, such as coloring matter listed in Appendix Tables I and II for tar-based coloring matter specified in the Ordinance of Ministry of Health and Welfare, Japan, e.g., Yellow No. 4, Blue No. 1, and Yellow No. 202-(1), and natural coloring matter permitted as food additives, e.g., chlorophyll, riboflavin, crocin, safflower, and anthraquinone; (d) vitamins, such as vitamin A, vitamin C, vitamin D, and vitamin E; (e) flavors; and (f) others, such as sulfur, precipitates of hot spring (i.e., flower of sulfur, calcareous tufa, siliceous sinter, etc.), mineral sands, powdered mica, neutral terra abla, roasted rice bran, antimicrobials, antiseptics, and other components necessary according to the preparation.

The bath composition of the present invention can be prepared from the above-mentioned essential components and up to 99% by weight of the above-mentioned optional components.

Water may be added to the bath composition of the present invention in an amount of from 0.01 to 90% by weight to increase preparation stability or to prepare an emulsified preparation.

The bath composition of the present invention can be formulated into various dose forms, such as powders, granules, tablets, liquids, and so on.

The bath composition of the present invention is poured into bath water in an amount to give a xanthine derivative concentration of from 0.1 to 200 ppm or to give a β-adrenergic stimulant concentration of from 0.01 to 200 ppm. If the xanthine derivative concentration of bath water is less than 0.1 ppm, the effects of giving a moist feel to the skin and a warm feel to the body cannot be obtained. Even if it exceeds 200 ppm, no further improvements in the moist or warm feel is brought about. If the β-adrenergic stimulant concentration of bath water is less than 0.01 ppm, the effects of giving a moist feel to the skin and a warm feel to the body cannot be obtained. Even if it exceeds 200 ppm, no further improvements in the moist or warm feel is brought about.

The present invention will now be illustrated in greater detail with reference to Examples, but it should be understood that the present invention is not deemed to be limited thereto.

EXAMPLES 1 TO 4 AND COMPARATIVE EXAMPLE 1

A liquid bath composition was prepared according to the formulation shown in Table 1 below in a conventional manner. The resulting bath composition was poured into a bath tub filled with 150 l of water at 40° C. Ten minutes later, the water was thoroughly stirred, and 5 panelists took a bath for 5 minutes each and judged the moist feel on the skin at the 10 minutes after the bathing, in accordance with the following rating standard:

5: The skin feels very moist.
4: The skin feels fairly moist.
3: The skin feels moist.
2: The skin feels slightly moist.
1: The same as the effect of a tap water bath.

The warm feel in the body at the 10 minutes after the bathing was also judged according to the following rating standard:

5: The body feels very warm.
4: The body feels fairly warm.
3: The body feels warm.
2: The body feels slightly warm.
1: The same as the effect of a tap water bath.

The results of judgement averaged are shown in Table 1.

TABLE 1

|  | Example | | | | Comparative Example |
|---|---|---|---|---|---|
|  | 1 | 2 | 3 | 4 | 1 |
| Formulation (wt %): | | | | | |
| Aminophylline | — | 3.0 | — | — | — |
| Theophylline | 0.4 | — | — | 0.4 | — |
| Caffeine | — | — | 1.0 | 0.6 | — |
| Ethanol | 10.0 | 10.0 | 10.0 | 10.0 | 10.0 |
| Glycerin | 20.0 | 20.0 | 20.0 | 20.0 | 20.0 |
| Purified water | 69.6 | 67.0 | 69.0 | 69.0 | 70.0 |
| Flavor | trace | trace | trace | trace | trace |
| Dose/bath (g) | 20 | 20 | 20 | 20 | 20 |
| Moist feeling | 3.6 | 4.0 | 3.8 | 3.8 | 1.2 |
| Warm feeling | 3.4 | 3.6 | 3.4 | 3.4 | 1.0 |

It is seen from Table 1 that the bath compositions of Examples 1 to 4 containing a xanthine derivative exhibit excellent performance in affording a moist feel to the skin and a warm feel to the body as compared with the comparative bath composition containing no xanthine derivative.

EXAMPLES 5 TO 8 AND COMPARATIVE EXAMPLES 2 AND 3

A powdered bath composition was prepared according to the formulation shown in Table 2 below in a conventional manner and tested in the same manner as in Example 1. The results obtained are shown in Table 2.

TABLE 2

|  | Example | | | | Comparative Example | |
| --- | --- | --- | --- | --- | --- | --- |
|  | 5 | 6 | 7 | 8 | 2 | 3 |
| Formulation (wt %): | | | | | | |
| Aminophylline | 3.0 | — | 0.2 | 0.4 | — | — |
| Caffeine | — | 1.0 | — | 0.8 | — | — |
| Sodium sulfate | 80.0 | 80.0 | 40.0 | 40.0 | 80.0 | 40.0 |
| Sodium hydrogencarbonate | 17.0 | 19.0 | 50.0 | 50.0 | 20.0 | 50.0 |
| Sodium carbonate | — | — | 9.8 | 8.8 | — | 10.0 |
| Flavor | trace | trace | trace | trace | trace | trace |
| Dose/bath (g) | 30 | 30 | 30 | 30 | 30 | 30 |
| Moist feel | 4.6 | 4.4 | 4.2 | 4.8 | 1.4 | 1.6 |
| Warm feel | 4.4 | 4.2 | 4.4 | 4.6 | 1.6 | 1.4 |

It is seen from Table 2 that the bath compositions of Examples 5 to 8 containing a combination of a xanthine derivative and inorganic salts exhibit excellent performance in affording a moist feel to the skin and a warm feel to the body as compared with the comparative bath compositions containing no xanthine derivative.

EXAMPLES 9 TO 12 AND COMPARATIVE EXAMPLE 4

A bath composition in the form of tablets was prepared according to the formulation shown in Table 3 below in a conventional manner and tested in the same manner as in Example 1. The results obtained are shown in Table 3.

TABLE 3

|  | Example | | | | Comparative Example |
| --- | --- | --- | --- | --- | --- |
|  | 9 | 10 | 11 | 12 | 4 |
| Formulation (wt %): | | | | | |
| Aminophylline | — | — | 5.0 | 0.2 | — |
| Theophylline | — | 1.4 | — | — | — |
| Caffeine | 0.5 | — | — | 0.2 | — |
| Sodium hydrogencarbonate | 45.5 | 44.6 | 41.0 | 45.6 | 46.0 |
| Sodium carbonate | 14.0 | 14.0 | 14.0 | 14.0 | 14.0 |
| Fumaric acid | 36.0 | 36.0 | 36.0 | 36.0 | 36.0 |
| Polyethylene glycol (6000) | 4.0 | 4.0 | 4.0 | 4.0 | 4.0 |
| Flavor | trace | trace | trace | trace | trace |
| Dose/bath (g) | 50 | 50 | 50 | 50 | 50 |
| Moist feeling | 4.6 | 4.8 | 4.8 | 4.6 | 3.2 |
| Warm feeling | 4.8 | 4.8 | 5.0 | 4.8 | 4.0 |

It is seen from Table 3 that the bath compositions of Examples 9 to 12 containing a combination of a xanthine derivative, an organic acid, and carbonates exhibit excellent performance in affording a moist feel to the skin and a warm feel to the body as compared with the comparative bath composition containing no xanthine derivative.

EXAMPLES 13 TO 16 AND COMPARATIVE EXAMPLE 5

A liquid bath composition was prepared according to the formulation shown in Table 4 below in a conventional manner and tested in the same manner as in Example 1. The results obtained are shown in Table 4.

TABLE 4

|  | Example | | | | Comparative Example |
| --- | --- | --- | --- | --- | --- |
|  | 13 | 14 | 15 | 16 | 5 |
| Formulation (wt %): | | | | | |
| Aminophylline | — | 1.0 | — | 0.2 | — |
| Theophylline | 0.3 | — | — | 0.1 | — |
| Caffeine | — | — | 0.8 | — | — |
| Glyceryl tri-octanoate | 39.7 | 39.0 | 39.2 | 39.7 | 40.0 |
| Trimyristin | 38.0 | 38.0 | 38.0 | 38.0 | 38.0 |
| Liquid paraffin | 10.0 | 10.0 | 10.0 | 10.0 | 10.0 |
| POE sorbitol fatty acid ester (40E.O.) | 9.0 | 9.0 | 9.0 | 9.0 | 9.0 |
| POE sorbitol fatty acid ester (20E.O.) | 3.0 | 3.0 | 3.0 | 3.0 | 3.0 |
| Flavor | trace | trace | trace | trace | trace |
| Dose/bath (g) | 20 | 20 | 20 | 20 | 20 |
| Moist feeling | 4.8 | 5.0 | 4.8 | 4.8 | 3.8 |
| Warm feeling | 4.2 | 4.4 | 4.4 | 4.2 | 1.4 |

It is seen from Table 4 that the bath compositions of Examples 13 to 16 containing a combination of a xanthine derivative and oily components exhibit excellent performance in affording a moist feel to the skin and a warm feel to the body as compared with the comparative bath composition containing no xanthine derivative.

EXAMPLE 17 AND COMPARATIVE EXAMPLE 6

A powdered bath composition was prepared according to the formulation shown in Table 5 below in a conventional manner and tested in the same manner as in Example 1. Further, the smell of the bath was evaluated in terms of the number of panelists who felt an offensive smell. The results obtained are shown in Table 5.

TABLE 5

|  | Example 17 | Comparative Example 6 |
| --- | --- | --- |
| Formulation (g): | | |
| Dried tea leaves | — | 12.0 |
| Caffeine | 0.24 | — |
| Sodium sulfate | 12.0 | 12.0 |
| Sodium hydrogencarbonate | 15.0 | 15.0 |
| Sodium carbonate | 2.76 | 2.76 |
| Flavor | trace | trace |
| Dose/bath (g) | 30 | 41.76 |
| Moist feeling | 4.2 | 4.0 |
| Warm feeling | 4.2 | 3.8 |
| Offensive smell | 0 | 5 |

It is seen from Table 5 that a bath containing dried leaves of a tea plant in an amount producing equal effects to the present invention gives off an offensive smell and is therefore unfavorable.

EXAMPLE 17 AND COMPARATIVE EXAMPLE 6

A powdered bath composition was prepared according to the formulation shown in Table 5 below in a conventional manner and tested in the same manner as in Example 1. Further, the smell of the bath was evaluated in terms of the number of panelists who felt an offensive smell. The results obtained are shown in Table 5.

EXAMPLES 18 TO 21 AND COMPARATIVE EXAMPLE 7

A liquid bath composition was prepared according to the formulation shown in Table 1 below in a conventional manner. The resulting bath composition was poured into a bath tub filled with 150 l of water at 40° C. Ten minutes later, the water was thoroughly stirred, and 5 panelists took a bath for 5 minutes each and judged the moist feel on the skin at the 10 minutes after the bathing, in accordance with the following rating standard:

5: The skin feels very moist.
4: The skin feels fairly moist.
3: The skin feels moist.
2: The skin feels slightly moist.
1: The same as the effect of a tap water bath.

The warm feel in the body at the 10 minutes after the bathing was also judged according to the following rating standard:

5: The body feels very warm.
4: The body feels fairly warm.
3: The body feels warm.
2: The body feels slightly warm.
1: The same as the effect of a tap water bath.

The results of judgement averaged are shown in Table 6.

TABLE 6

| | Example | | | | Comparative Example |
|---|---|---|---|---|---|
| | 18 | 19 | 20 | 21 | 7 |
| Formulation (wt %): | | | | | |
| Isoproterenol hydrochloride | — | 2.0 | — | — | — |
| Dobutamine hydrochloride | 0.5 | — | — | 0.6 | — |
| Salbutamol sulfate | — | — | 1.2 | 0.4 | — |
| Ethanol | 10.0 | 10.0 | 10.0 | 10.0 | 10.0 |
| Glycerin | 20.0 | 20.0 | 20.0 | 20.0 | 20.0 |
| Purified water | 69.5 | 68.0 | 68.8 | 69.0 | 70.0 |
| Flavor | trace | trace | trace | trace | trace |
| Dose/bath (g) | 20 | 20 | 20 | 20 | 20 |
| Moist feel | 3.8 | 4.0 | 3.8 | 3.6 | 1.0 |
| Warm feel | 3.6 | 3.8 | 3.6 | 3.8 | 1.2 |

It is seen from Table 6 that the bath compositions of Examples 18 to 21 containing a β-adrenergic stimulant exhibit excellent performance in affording a moist feel to the skin and a warm feel to the body as compared with the comparative bath composition containing no β-adrenergic stimulant.

EXAMPLES 22 TO 25 AND COMPARATIVE EXAMPLES 8 AND 9

A powdered bath composition was prepared according to the formulation shown in Table 7 below in a conventional manner and tested in the same manner as in Example 18. The results obtained are shown in Table 7.

TABLE 7

| | Example | | | | Comparative Example | |
|---|---|---|---|---|---|---|
| | 22 | 23 | 24 | 25 | 8 | 9 |
| Formulation (wt %): | | | | | | |
| Isoproterenol hydrochloride | 3.0 | — | 0.4 | 0.2 | — | — |
| Salbutamol sulfate | — | 0.8 | — | 1.0 | — | — |
| Sodium sulfate | 80.0 | 80.0 | 40.0 | 40.0 | 80.0 | 40.0 |
| Sodium hydrogencarbonate | 17.0 | 19.2 | 50.0 | 50.0 | 20.0 | 50.0 |
| Sodium carbonate | — | — | 9.6 | 8.8 | — | 10.0 |
| Flavor | trace | trace | trace | trace | trace | trace |
| Dose/bath (g) | 30 | 30 | 30 | 30 | 30 | 30 |
| Moist feel | 4.4 | 4.6 | 4.4 | 4.6 | 1.6 | 1.8 |
| Warm feel | 4.2 | 4.4 | 4.6 | 4.4 | 1.6 | 1.6 |

It is seen from Table 7 that the bath compositions of Examples 22 to 25 containing a combination of a β-adrenergic stimulant and inorganic salts exhibit excellent performance in affording a moist feel to the skin and a warm feel to the body as compared with the comparative bath compositions containing no β-adrenergic stimulant.

EXAMPLES 26 TO 29 AND COMPARATIVE EXAMPLE 10

A bath composition in the form of tablets was prepared according to the formulation shown in Table 8 below in a conventional manner and tested in the same manner as Example 18. The results obtained are shown in Table 8.

TABLE 8

| | Example | | | | Comparative Example |
|---|---|---|---|---|---|
| | 26 | 27 | 28 | 29 | 10 |
| Formulation (wt %): | | | | | |
| Isoproterenol hydrochloride | — | — | 4.0 | 0.4 | — |
| Dobutamine hydrochloride | — | 2.0 | — | — | — |
| Salbutamol sulfate | 0.6 | — | — | 0.2 | — |
| Sodium hydrogencarbonate | 45.4 | 44.0 | 42.0 | 45.4 | 46.0 |
| Sodium carbonate | 14.0 | 14.0 | 14.0 | 14.0 | 14.0 |
| Fumaric acid | 36.0 | 36.0 | 36.0 | 36.0 | 36.0 |
| Polyethylene glycol (Molecular weight: 6,000) | 4.0 | 4.0 | 4.0 | 4.0 | 4.0 |
| Flavor | trace | trace | trace | trace | trace |
| Dose/bath (g) | 50 | 50 | 50 | 50 | 50 |
| Moist feel | 4.8 | 4.8 | 4.6 | 4.8 | 3.2 |
| Warm feel | 4.8 | 5.0 | 5.0 | 4.8 | 3.8 |

It is seen from Table 8 that the bath compositions of Examples 26 to 29 containing a combination of a β-adrenergic stimulant, an organic acid, and carbonates exhibit excellent performance in affording a moist feel to the skin and a warm feel to the body as compared with the comparative bath composition containing no β-adrenergic stimulant.

EXAMPLES 30 TO 33 AND COMPARATIVE EXAMPLE 11

A liquid bath composition was prepared according to the formulation shown in Table 9 below in a conventional manner and tested in the same manner as in Example 18. The results obtained are shown in Table 9.

TABLE 9

|  | Example | | | | Comparative Example |
|---|---|---|---|---|---|
|  | 30 | 31 | 32 | 33 | 11 |
| Formulation (wt %): | | | | | |
| Isoproterenol hydrochloride | — | 0.8 | — | 0.1 | — |
| Dobutamine hydrochloride | 0.2 | — | — | 0.2 | — |
| Salbutamol sulfate | — | — | 1.0 | — | — |
| Glyceryl tri-octanoate | 39.8 | 39.2 | 39.0 | 39.7 | 40.0 |
| Octyldodecyl myristate | 38.0 | 38.0 | 38.0 | 38.0 | 38.0 |
| Liquid paraffin | 10.0 | 10.0 | 10.0 | 10.0 | 10.0 |
| POE sorbitol fatty acid ester (40E.O.) | 9.0 | 9.0 | 9.0 | 9.0 | 9.0 |
| POE sorbitol fatty acid ester (20E.O.) | 3.0 | 3.0 | 3.0 | 3.0 | 3.0 |
| Flavor | trace | trace | trace | trace | trace |
| Dose/bath (g) | 20 | 20 | 20 | 20 | 20 |
| Moist feel | 4.8 | 4.8 | 5.0 | 4.8 | 3.8 |
| Warm feel | 4.2 | 4.2 | 4.4 | 4.4 | 1.4 |

It is seen from Table 9 that the bath compositions of Examples 30 to 33 containing a combination of a β-adrenergic stimulant and oily components exhibit excellent performance in affording a moist feel to the skin and a warm feel to the body as compared with the comparative bath composition containing no β-adrenergic stimulant.

EXAMPLES 34 TO 46

A liquid, powdered or tablet bath composition was prepared according to the formulation shown in Table 10 below in a conventional manner and the resulting bath composition was poured into a bath tub filled with 150 l of water at 40° C. Ten minutes later, the water was thoroughly stirred, and 5 panelists took a bath for 5 minutes each and judged the warm feel in the body at the 10 minutes and 60 minutes after the bathing, in accordance with the following rating standard:

5: The body feels very warm.
4: The body feels fairly warm.
3: The body feels warm.
2: The body feels slightly warm.
1: The same as the effect of a tap water bath.

The results of judgement averaged are shown in Table 10.

TABLE 10

(Liquid Bath composition)

|  | EXAMPLE | | | | |
|---|---|---|---|---|---|
|  | 34 | 35 | 36 | 37 | 38 |
| Formulation (wt %): | | | | | |
| Aminophylline | 3.0 | — | — | 1.5 | — |
| Theophylline | — | 0.4 | — | — | 0.2 |
| Isoproterenol hydrochloride | — | — | 2.0 | 1.0 | 1.0 |
| Ethanol | 10.0 | 10.0 | 10.0 | 10.0 | 10.0 |
| Glycerin | 20.0 | 20.0 | 20.0 | 20.0 | 20.0 |
| Purified water | 67.0 | 69.6 | 68.0 | 67.5 | 68.8 |
| Flavor | trace | trace | trace | trace | trace |
| Dose/bath (g) | 20 | 20 | 20 | 20 | 20 |
| Warm feeling: | | | | | |
| after 10 minutes | 3.6 | 3.4 | 3.8 | 4.0 | 4.2 |
| after 60 minutes | 1.4 | 1.2 | 1.4 | 3.0 | 3.2 |

(Powdered Bath composition)

|  | EXAMPLE | | | | |
|---|---|---|---|---|---|
|  | 39 | 40 | 41 | 42 | 43 |
| Formulation (wt %): | | | | | |
| Aminophylline | 3.0 | — | — | 1.0 | — |
| Caffeine | — | 0.5 | — | — | 0.2 |
| Isoproterenol hydrochloride | — | — | 3.0 | 1.0 | 1.0 |
| Sodium sulfate | 80.0 | 80.0 | 80.0 | 80.0 | 80.0 |
| Sodium hydrogen-carbonate | 17.0 | 19.5 | 17.0 | 18.0 | 18.8 |
| Flavor | trace | trace | trace | trace | trace |
| Dose/bath (g) | 30 | 30 | 30 | 30 | 30 |
| Warm feeling: | | | | | |
| after 10 minutes | 4.4 | 4.2 | 4.2 | 4.6 | 4.4 |
| after 60 minutes | 2.2 | 1.8 | 2.0 | 3.8 | 3.6 |

(Tablet Bath composition)

|  | EXAMPLE | | |
|---|---|---|---|
|  | 44 | 45 | 46 |
| Formulation (wt %): | | | |
| Aminophylline | 5.0 | — | 2.0 |
| Isoproterenol hydrochloride | — | 4.0 | 1.0 |
| Sodium hydrogen-carbonate | 41.0 | 42.0 | 43.0 |
| Sodium carbonate | 14.0 | 14.0 | 14.0 |
| Fumaric acid | 36.0 | 36.0 | 36.0 |
| Polyethylene glycol (6000) | 4.0 | 4.0 | 4.0 |
| Flavor | trace | trace | trace |
| Dose/bath (g) | 30 | 30 | 30 |
| Warm feeling: | | | |
| after 10 minutes | 5.0 | 5.0 | 5.0 |
| after 60 minutes | 3.8 | 3.6 | 4.2 |

It is seen from Table 10 that the bath compositions containing both of a xanthine derivative and a β-adrenergic stimulant exhibit excellent performance in affording a long-lasting warm feel to the body.

While the invention has been described in detail and with reference to specific examples thereof, it will be apparent to one skilled in the art that various changes and modifications can be made therein without departing from the spirit and scope thereof.

What is claimed is:

1. A method for imparting a moist feel to the skin and improving a warm feel of the body, which comprises bathing the body in a bath containing a bathing composition comprising at least one of a xanthine or a β-adrenergic stimulant in an amount effective to achieve the functions of imparting a moist feel to the skin and improving a warm feel of the body.

2. A method comprising bathing the body in a bath containing a bathing composition comprising at least one of a xanthine or a β-adrenergic stimulant in an amount effective to achieve the functions of imparting a moist feel to the skin and improving a warm feel of the body, wherein said xanthine is represented by formula (I):

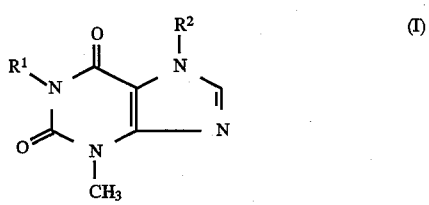

wherein $R^1$ represents a methyl group or a hydrogen atom; $R^2$ represents a hydrogen atom or an alkyl group having 1 to 12 carbon atoms which may be substituted by one or two hydroxyl groups or alkanoyl groups having 2 to 10 carbon atoms, and salts thereof.

3. The method of claim 1, wherein said xanthine is at least one compound selected from the group consisting of xanthine, aminophylline, theophylline, choline theophylline, caffeine, theobromine, oxtriphylline, diprophylline, and proxyphylline.

4. The method of claim 1, wherein said xanthine is at least one compound selected from the group consisting of aminophylline, theophylline, and caffeine.

5. The method of claim 1, wherein said β-adrenergic stimulant is at least one compound selected from the group consisting of isoproterenol, epinephrine, dl-norepinephrine, dobutamine, dopamine, butopamine, salbutamol, terbutaline, isoetarine, protokylol, fenoterol, metaproterenol, clorprenaline, hexoprenaline, trimethoquinol, procaterol hydrochloride, prenalterol, forskolin, disodium (R,R)-5-[2-[[2-(3-chlorophenyl)-2-hydroxyethyl]amino]-propyl]-1,3-benzodioxol-2,2-dicarboxylate, (R*,R*)-4-[2-({2-[(3-chlorophenyl)-2-hydroxyethyl]amino}propyl)phenyl]phenoxy-acetic acid, {2-hydroxy-5-[2-({2-hydroxy-3-[4-(1-methyl-4trifluoromethyl)-1H-imidazol-2-yl]phenoxy}propyl)amino]-ethoxy}benzamide monomethanesulfonate, and erythro-DL-1-(7-methylindan-4-yloxy)-3-isopropylaminobutan-2-ol, and pharmaceutically acceptable salts thereof.

6. The method of claim 1, wherein said β-adrenergic stimulant is isoproterenol, dobutamine, salbutamol, or pharmaceutically acceptable salts thereof.

7. The method of claim 1, wherein said xanthine is present in an amount to give a concentration in bath water of from 0.1 to 200 ppm and said β-adrenergic stimulant is present in an amount to give a concentration in bath water of from 0.01 to 200 ppm.

8. The method of claim 1, wherein the composition further contains an inorganic salt in an amount to give a concentration in bath water of from 10 to 2,000 ppm.

9. The method of claim 8, wherein the composition contains a carbonate, as said inorganic salt, and further an organic acid in amounts to evolve carbon dioxide gas in bath water at a carbon dioxide gas concentration of 60 ppm or more.

10. The method of claim 1, wherein the composition further contains an oily component in an amount to give a concentration in bath water of from 10 to 500 ppm.

* * * * *